United States Patent
Tomita

(10) Patent No.: US 8,683,879 B2
(45) Date of Patent: Apr. 1, 2014

(54) SAMPLE INJECTING DEVICE

(75) Inventor: Masami Tomita, Kyoto Pref. (JP)

(73) Assignee: Shimadzu Corporation, Kyoto (JP)

( * ) Notice: Subject to any disclaimer, the term of this patent is extended or adjusted under 35 U.S.C. 154(b) by 582 days.

(21) Appl. No.: 13/029,372

(22) Filed: Feb. 17, 2011

(65) Prior Publication Data

US 2011/0209565 A1 Sep. 1, 2011

(30) Foreign Application Priority Data

Feb. 26, 2010 (JP) .................................. 2010-041627

(51) Int. Cl.
*G01N 30/24* (2006.01)
*G01N 30/20* (2006.01)
*G01N 35/10* (2006.01)
*B08B 9/00* (2006.01)

(52) U.S. Cl.
CPC ............... *G01N 30/24* (2013.01); *G01N 30/20* (2013.01); *G01N 35/1011* (2013.01)
USPC .................... 73/864.21; 73/61.55; 73/863.01; 73/864.22; 73/864.25; 73/864.84; 73/864.87; 134/166 R

(58) Field of Classification Search
CPC ... G01N 30/20; G01N 30/24; G01N 35/1011; G01N 2030/201; G01N 2030/202
USPC .......... 73/61.55–61.56, 61.59, 64.56, 863.01, 73/864.21–864.22, 864.24–864.25, 73/864.83–864.84, 864.87; 134/166 R
See application file for complete search history.

(56) References Cited

U.S. PATENT DOCUMENTS

| | | | | |
|---|---|---|---|---|
| 5,783,742 A | * | 7/1998 | Shibamoto et al. | ........... 73/23.41 |
| 8,234,939 B2 | * | 8/2012 | Maeda et al. | ............... 73/864.21 |
| 8,580,210 B2 | * | 11/2013 | Katsumi et al. | ..... G01N 35/1011 |
| 2009/0090173 A1 | * | 4/2009 | Fukuda et al. | ............... 73/61.55 |
| 2010/0206411 A1 | * | 8/2010 | Maeda et al. | ............ 137/625.17 |
| 2013/0243653 A1 | * | 9/2013 | Koiso et al. | .................. 422/68.1 |

FOREIGN PATENT DOCUMENTS

| | | |
|---|---|---|
| JP | 06-148157 | 5/1994 |
| JP | 10-170488 | 6/1998 |
| JP | 10-281948 | 10/1998 |
| JP | 2005-134217 | 5/2005 |
| JP | 4085954 | 2/2008 |
| WO | 2009041441 | 4/2009 |
| WO | 2009041442 | 4/2009 |

OTHER PUBLICATIONS

"Office Action of China Counterpart Application", issued on May 24, 2013, with English translation thereof, pp. 1-16.

\* cited by examiner

*Primary Examiner* — Thomas P Noland
(74) *Attorney, Agent, or Firm* — J. C. Patents

(57) ABSTRACT

A sample injecting device is provided for reducing carryover. The sample injecting device includes the following mode: a needle is set at a low descending speed when sample is injected into an injection port in a total-volume injection manner by the sample injecting device. When the needle is in contact with the injection port, the needle is set at a low speed, thereby increasing the accuracy of the position of the needle relative to an injection hole and decreasing friction between the needle and the injection hole. Contaminants present in the injection hole are prevented from easily flowing from the injection hole into an analyzing flow path, so as to achieve an excellent low carryover.

5 Claims, 3 Drawing Sheets

| Mode | Cleaning procedures | | Speed of needle [mm/sec] |
|---|---|---|---|
| | Outer surface of needle | Inner surface of needle | |
| 1 | × | × | 50 |
| 2 | ○ | × | 50 |
| 3 | ○ | ○ | 5 |

SAMPLE INJECTING DEVICE

CROSS-REFERENCE TO RELATED APPLICATION

This application claims the priority benefit of Japan patent application serial no. 2010-041627, filed on Feb. 26, 2010. The entirety of the above-mentioned patent application is hereby incorporated by reference herein and made a part of the specification.

BACKGROUND OF THE INVENTION

1. Field of the Invention

The present invention relates to a sample injecting device for importing a liquid sample into an analysis apparatus, in particular, to a sample injecting device including a needle, connected to a flow path switching valve, and a port.

2. Description of Related Art

In order to analyze multiple samples, a sample-injecting device for automatically introducing the sample into an analysis apparatus such as a liquid chromatograph in a defined sequence has already been used. FIG. 5 (*a*) is a schematic view of a liquid chromatograph. The liquid chromatograph includes a liquid delivery device 10, a sample injecting device 20, a separating and detecting unit 30, and a controlling and parsing unit 40, wherein the sample injecting device 20 is disposed between the liquid delivery device 10 and the separating and detecting unit 30. The separating and detecting unit 30 includes an analytical column 31 or a detector 32, and forms various flow paths corresponding to different analytical aims; and the separating and detecting unit 30 functions as an analyzing unit. The liquid delivery device 10, the sample injecting device 20, and the separating and detecting unit 30 are controlled by the controlling and parsing unit 40. Furthermore, the controlling and parsing unit 40 receives signals from the detector 32, parses the sample in a qualitative and quantitative manner, saves the parsed data or generates an analysis report and outputs the analysis report.

The sample injecting device has two injection modes: "total-volume injection", in which all measured sample is injected from a sample vial, and "loop injection", in which a part of the measured sample is injected into a sample loop from a sample vial (Patent Document 1 and Patent Document 2 etc.). In the field where only an extremely low amount of sample can be extracted, in order to analyze the extracted sample without any waste, the sample injecting device of total-volume injection has been widely used.

FIG. 5 (*b*) is a schematic view of internal flow paths in a sample injecting device 20 of total-volume injection. The sample injecting device 20 forms flow paths with a six-port two-position valve 21 and a six-position valve 22 as the center. The flow path of the mobile phase solution from the liquid delivery device 10 to the sample injecting device 20 is firstly connected to one port of the six-port two-position valve 21. Starting from the sample loop 23, passing through a needle 24 disposed at the front end of the sample loop 23, and then through an injection port 25 with the needle 24 inserted therein, the flow path from the upstream side of a liquid delivery device 10 is communicated with a flow path towards the separating and detecting unit 30 of the downstream side. Thus, all sample filled in the needle 24 to the sample loop 23 is introduced into the separating and detecting unit 30. A flow path communicated with a cleaning liquid container, a flow path communicated with a measuring pump 26, and a flow path communicated with a cleaning port 27 are connected on the six-position valve 22, wherein the measuring pump 26 sucks in the cleaning liquid from the cleaning liquid container or sucks in the sample from the sample vial 28; the cleaning port 27 is provided for the insertion of the needle 24 so as to clean the needle; furthermore, the needle 24 is communicated with the flow paths of the sample loop 23 and the measuring pump 26 through the six-port two-position valve 21 (Patent Document 3 and Patent Document 4, etc.).

When the sample is injected into an injection unit, the front end of the needle is lowered so that the front end of the needle is inserted into a correct position of the injection port (flow path hole). However, in circumstances when the front end of the needle is not lowered to the correct position of the port, the front end of the needle is worn, or the injection port is contaminated by the front end of the needle. Thus, the position of the needle must be adjusted so that the needle is lowered to the correct position of the injection port. However, recently in order to increase throughput of analysis, the action speed of the needle becomes higher. Therefore, it is necessary to make correct adjustments to the position of the needle. Patent Document 5 provides the following technology: position alignment is carried out at a speed slower than that of a common action, and then, the upward and downward actions are repeated for many times at a common speed (aging actions), so that the position relation of the needle and the injection port is memorized in the device.

Therefore, after the needle is squeezed into the injection port, the sample injecting device maintains a watertight state. However, in order to maintain the needle and the injection port in a watertight manner, materials with a low mechanical strength are generally used to faun one of the needle and the injection port, so as to maintain the sealed state through such design. In most circumstances, the needle has to perforate the hood of the sample vial, and thus, the needle uses a hard material (for example, stainless steel as a base material), and the port uses a relatively soft material (for example, polyetheretherketone (PEEK) and resin).

DOCUMENTS IN THE PRIOR ART

Patent Documents

[Patent Document 1] Japanese Patent Laid-open Gazette No. H6-148157.
[Patent Document 2] Japanese Patent Laid-open Gazette No. H10-170488.
[Patent Document 3] International Publication Pamphlet No. 09/041,441.
[Patent Document 4] International Publication Pamphlet No. 09/041,442.
[Patent Document 5] Japanese Patent No. 4085954.

In circumstances when the needle and the injection port are sealed, after the needle is vertically squeezed into the flow path hole of the injection port, the flow path hole is slightly expanded as the times of squeezing increase. However, if different positions are squeezed, an indentation generated by the needle is formed on the taper surface. Therefore, the watertight state of the indentation cannot be ensured. Especially in the case of total-volume injection, a flow path communicating with the liquid delivery device, the sample loop, the needle, the injection port, and the column is formed, so if the liquid delivery pressure of the liquid delivery device becomes higher, the following significant problem will arise; that is, the liquid is leaked from the joint of the needle and the injection port.

Furthermore, when the needle is inserted into the sample vial, sample constituents will be attached on the surface of the needle. If the needle in this state is inserted into the injection port, the sample constituents will be attached on the injection hole of the injection port, and at the next injection, the attachments are injected together with the sample, so as to generate the so-called "carryover phenomenon". The carryover phenomenon is defined as follows: a part of the injected sample is left over, which affects the next analysis. Although through the treatment of the needle surface, the cleaning of the needle, and the changing of the shape of the injection port, the carryover can be greatly improved, problems still arise. Moreover, recently as a result of an extremely micro analysis and high sensitivity of detection, the problems become even more severe. Therefore, the carryover is a reason of preventing correct analysis of the quantity of the sample extracted from the sample vial.

If the needle is lowered to a position deviating from the flow path hole of the injection port, the needle descends in a manner of slipping on the taper surface of the injection port and forms a watertight state with the flow path hole. However, as described above, the outer surface of the needle is contaminated by the sample at this moment; and thus, when the needle slips on the taper surface, the injection port is also contaminated by the sample. At the next injection, the contaminants are in friction against the needle and are squeezed into the flow path hole, and thus, the following problem arises, in which significant carryover occurs.

SUMMARY OF THE INVENTION

Accordingly, the present invention is directed to a sample injecting device. The sample injecting device includes: a sample loop for sample measurement, including a needle for sample injection at a front end; an injection port having an opening for insertion of the vertically descending needle, and injecting the sample drawn in by the needle into an analyzing flow path; a setting unit for selecting from multiple alternative speeds a speed of the needle moving from a defined position to the injection port when the sample is injected; and a controlling unit for controlling the movement of the needle according to the selected moving speed of the needle.

The sample injecting device further includes: a cleaning mechanism for cleaning the needle, and a cleaning procedure-setting unit for setting the cleaning procedures of the cleaning mechanism.

Moreover, the moving speed of the needle is determined by setting the cleaning procedures.

Alternatively, as one of the conditions for analyzing the sample, the moving speed of the needle is set.

Preferably, the moving speed of the needle during the movement from the defined position to the port is lower when the needle is close to one side of the injection port.

Effects of the Invention

By slowing the descending speed of the needle, deviations caused by mechanical clearance of a descending mechanism of the needle can be eliminated without changing other structures of the sample injecting device; and the position of the needle which descends to the injection port can be maintained at a fixed position. Even if the liquid is delivered to a mobile phase under a high pressure, the occurrences of a leak or carryover of the liquid at the injection port can be reduced.

If the speed of the needle is set to be reduced before the needle abuts against the injection port, it costs a shorter time for the needle to move within the distance from the defined position (just above the injection port) to the injection port, and the needle can be inhibited at a lower moving speed when the needle abuts against the injection port.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF THE EMBODIMENTS

The present invention is hereinafter described in detail with reference to the accompanying drawings.

Figures 1, 2:
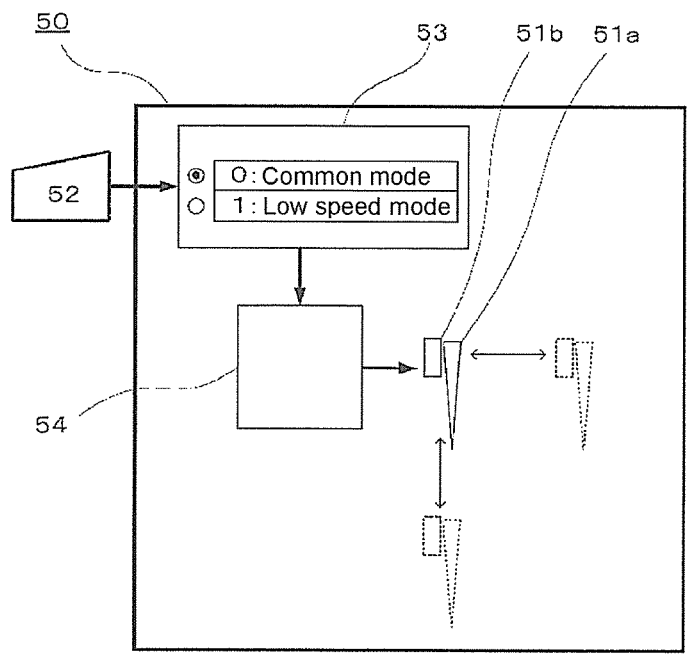
FIG. 1 illustrates a sample injecting device according to the present invention exemplarily.
FIG. 2 shows an example of a combination of setting the descending speed of the needle corresponding to the cleaning procedures.

FIG. 1 illustrates a sample injecting device according to the present invention exemplarily. The sample injecting device 50 includes a needle 51a for drawing in sample or ejecting the sample; a driving mechanism 51b of the needle 51a; an inputting unit 52 for inputting various conditions that make the sample injecting device 50 operate; a needle action setting unit 53 for setting the actions of the needle; and a needle action controlling unit 54 for controlling the actions of the needle according to the set action conditions. In order to carry out an analysis, the sample injecting device 50 further includes a flow path switching valve or a sample loop, and these components are the same as conventional components.

A plurality of alternative modes such as "common mode" and "low speed mode" is pre-stored in the needle action-setting unit 53 for convenient selection of a user. As an example for description, if the "common mode" is set as 50 mm/sec and the "low speed mode" is set as about 5 mm/sec, the "common mode" refers to an action speed equivalent to that of the conventional device and the "low speed mode" refers to an action speed which is one tenth of the "common mode".

After the user operates the inputting unit 51 and selects the "common mode" or the "low speed mode", the needle is set to descend from the defined position above the port to the injection port at a speed corresponding to the selected mode. In FIG. 1, in order to indicate the selection clearly, a radio button is used for selecting the mode. However, three or more modes may also be used as long as any one of the modes can be specified. If the modes are pre-marked with an appropriate identifier such as a number or alphabet, the identifiers can be conveniently processed as parameters in the processing of device-side.

Moreover, the speed of the needle corresponding to the modes is unnecessarily set as a fixed value, and instead, can be changed in a manner without setting the descending speed of the needle too small. The speed of the needle can be frequently changed corresponding to the mechanical deviation.

The needle action-controlling unit 54 is used for directing the actions of the needle 51a towards the driving mechanism 51b. Thus, according to an analysis schedule, the needle action controlling unit 54 can direct the needle 51a to draw in the sample and cause the needle 51a to move to above the injection port and then to descend to the port at a set speed.

The "common mode" is applicable to the following analysis: even if a deviation occurs to the descending position of the needle, the analysis time can be shortened by increasing the descending speed. The "low speed mode" is directed to an analysis with high-pressure liquid delivery or low carryover.

Furthermore, the descending speed of the needle in the entire range from the defined position to the injection port is not required to be constant. If the needle is switched to a low speed action before the needle abuts against the injection port, the time for the needle to move in the range can be shortened to be closed to that in the "common mode", even the needle-action setting unit is in the "low speed mode".

It is unnecessary to set the descending speed of the needle according to a value of the distance/time dimension. For example, if a pulse motor is used to drive the needle, it is evident that the speed can be set as the number of pulses per unit time.

As an aspect of the present invention, as the movement of the needle towards the sample vial or the inside of the surface above the cleaning port, or the intake of the sample, and the actions of the cleaning procedures remain unchanged, and as long as the descending speed of the needle is set to a low speed, an analysis with high-pressure liquid delivery or low carryover is achieved.

An analysis device using the sample injecting device is used to analyze multiple samples automatically in sequence according to an analysis schedule. During a period of the analysis schedule, it is unnecessary to carry out actions in the same mode. As one of the analytical conditions of various analyses, the descending speed of the needle is preferably preset.

The present invention mainly focuses on setting the speed to a low speed at the moment when the needle abuts against the injection port, and thus, can be used together with other related techniques. The following technique has already been provided in International Patent Application PCT/JP2009/004408 in reference to the actions of the needle on the injection port; that is, the injection port is cleaned by ejecting a cleaning liquid from the needle or drawing in the cleaning liquid from the needle. The cleaning procedures provided in the international patent application is related to the selection of the descending speed of the needle in the present invention.

FIG. 2 shows an example of a combination of setting the cleaning procedures and the descending speed of the needle in a related manner.

The "cleaning procedures" are parameters related to selection between cleaning the outer surface of the needle at the cleaning port and cleaning the inner surface of the needle at the injection port; and the "speed of the needle" is a parameter related to the descending speed of the needle descending from the defined position above the injection port to the injection port. For example, if the mode 2 is selected, the following conditions are set, that is, clean the outer surface of the needle at the cleaning port, do not clean the inner surface of the needle at the injection port, and set the descending speed of the needle to 50 mm/sec. The "cleaning the outer surface of the needle" herein refers to cleaning the needle by dipping the needle into the cleaning port before or after the sample is drawn into the needle; and the "cleaning the inner surface of the needle" refers to cleaning a flow path or an area around the injection hole of the injection port before the sample is drawn into the needle, wherein the flow path measures the quantity of the extracted sample. The content related to the "cleaning the outer surface of the needle" is described in detail in Japanese Patent Gazette No. 3826891; and the content related to the "cleaning the inner surface of the needle" is described in detail in International Patent Application PCT/JP2009/004408. Therefore, a brief description is given in advance here.

The user operates the inputting unit and selects the required mode from the needle action setting unit, so as to set the cleaning procedures, related to the injection, and the action speed of the needle.

Besides setting by the user directly through the inputting unit, as for the liquid chromatograph including the sample injecting device of the present invention, the setting can also be carried out through the controlling and parsing unit which controls the entire system.

EXAMPLE

To reduce the carryovers, the sample injecting device of the present invention has the structure and actions as described above.

An example of actual measurement is illustrated on how to achieve the effects of reducing the carryover through the sample injecting device of the present invention. In order to indicate the quantity of the carryovers, caffeine aqueous solution is used as the sample for analysis. An area a of the peak of the chromatogram of the caffeine aqueous solution is obtained. Then, the liquid (blank specimen) with the same constituents as that of the mobile phase solution is analyzed to calculate an area $\beta$ of the peak appearing in the same hold time as that of the caffeine aqueous solution. And then, the ratio of $\beta$ to $\alpha$ is set as the quantity of the carryover. Corresponding to the "common mode" and the "low speed mode" of the sample injecting device of the present invention, the analysis is carried out according to the following analytical conditions.

[Analytical Conditions]

| | |
|---|---|
| Sample | Caffeine Aqueous Solution |
| Amount of Sample Injection | 5 μL |
| Composition of Mobile Phase | Water:Methanol = 7:3 |
| Flow Rate | 0.3 mL/min (Liquid Delivery Pressure: 90 MPa) |
| Column | Reverse Phase Column (Inner Diameter 1.5 mm × Length 100 mm) |
| Detector | Ultraviolet-visible Spectrophotometric Detector (Detection Wavelength: 272 nm) |

Figure 4:
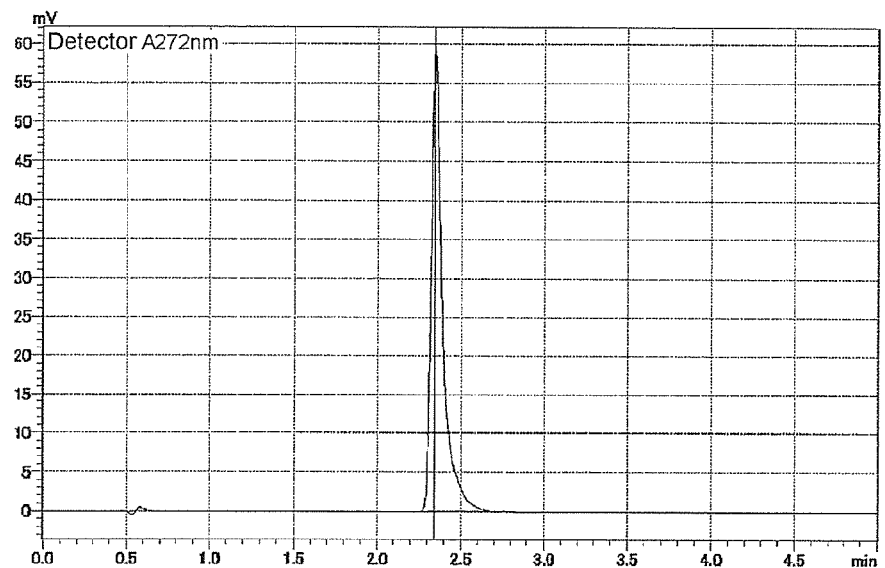
FIG. 4 is a chromatogram of a caffeine solution for evaluation of the blank tests.
Figure 5A:
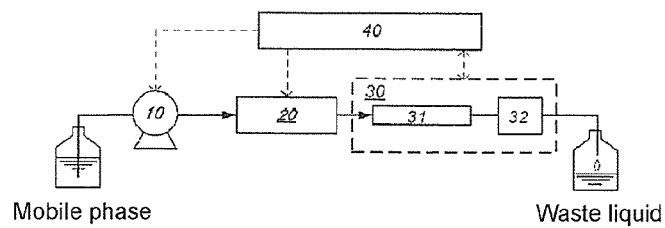
FIG. 5(a) and FIG. 5(b) are schematic views of structures of the liquid chromatograph and the sample injecting device.
Figure 5B:
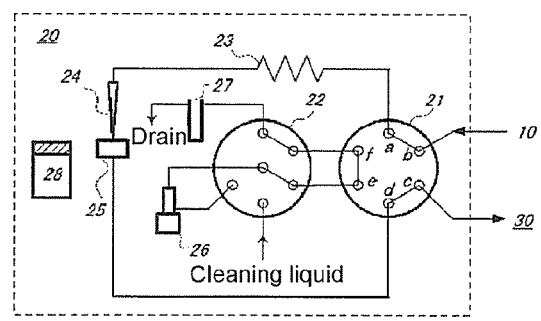

FIG. 4 is a chromatogram of the caffeine aqueous solution with a concentration of 20 mg/L obtained by the liquid chromatograph including the sample injecting device of the present invention. It is determined that the peak of the caffeine appears at a position where the hold time is 2.34 minutes. During the analysis of the blank sample, the peak appearing at the hold time is the peak of the caffeine.

Figure 3A:
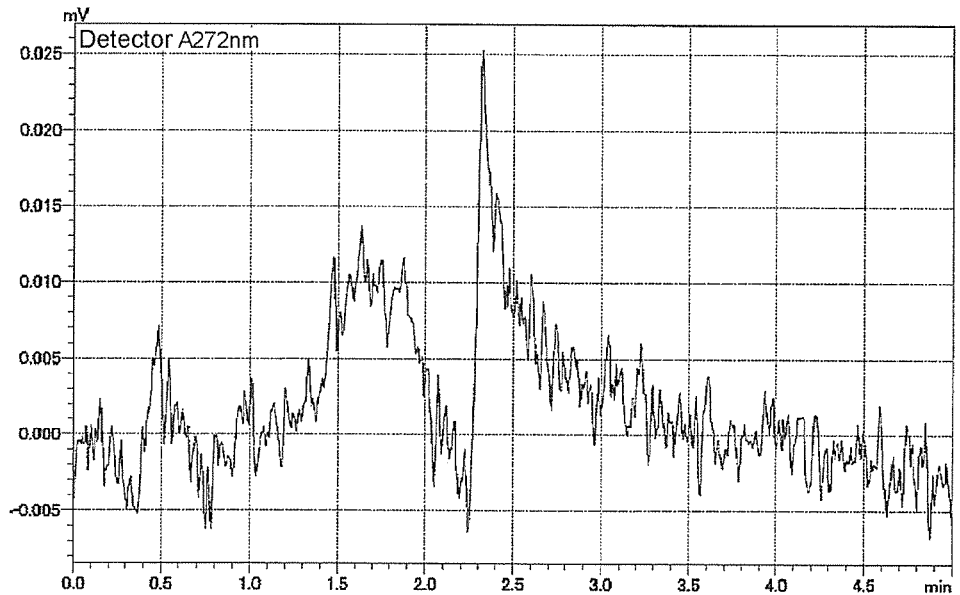
FIG. 3(a) and FIG. 3(b) are chromatograms of blank tests carried out by the sample injecting device of the present invention in a low speed mode and in a common mode.
Figure 3B:
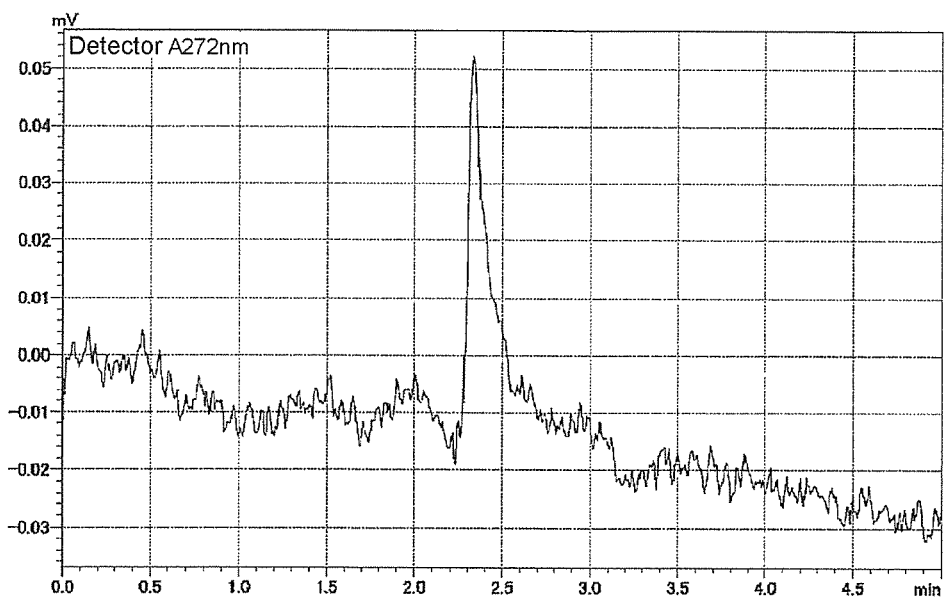

FIG. 3 (a) and FIG. 3 (b) respectively are chromatograms of the blank sample, in which FIG. 3 (a) is a chromatogram based on the "low speed mode" and FIG. 3 (b) is a chromatogram based on the "common mode". In the chromatograms of FIGS. 3(a) and 3(b), the horizontal axis is the time axis and the horizontal axes of both chromatograms have the same scales; however, the longitudinal axis is the strength axis of the detection signal, the scale in FIG. 3 (a) is about a half of the scale in FIG. 3 (b).

Furthermore, for the blank sample after the analysis of the 20 mg/L caffeine aqueous solution, the peak of the caffeine is not detected (below the detection limit of the detector), and thus, the blank sample is analyzed after a 2000 mg/L caffeine aqueous solution, which is a hundred times of the 20 mg/L caffeine aqueous solution, is injected so as to evaluate the carryover generated by the blank sample.

It is shown in FIG. 4 that the area a of the peak is 273161, and the area β of the peak corresponding to the detected caffeine during the analysis of the blank sample is 144 under the "low speed mode" (the quantity of the carryover β/α is 0.0005%) and 598 under the "common mode" (the quantity of the carryover β/α is 0.0022%). That is, it is shown that the "low speed mode" of the sample injecting device of the present invention achieves lower carryover.

As described above, the sample injecting device of the present invention reduces the carryover significantly. In the description of the present invention, the flow path between the injection port 25 and the high-pressure valve 21 is long in the drawings, so as to prevent the cross of the flow paths in the drawings. To shorten the analysis time or reduce the dead volume, it is better that the flow path is short. And similar to the invention disclosed in Japanese Patent Laid-open Gazette No. 2004-215118, the invention of directly disposing the injection port 25 at the port of the high-pressure valve 21 also exists. Furthermore, although it is clearly shown in the drawings that the sample loop 23 includes a spiral unit, similar to the invention disclosed in Japanese Patent Laid-open Gazette No. 2004-85499, the invention not including a spiral unit and ensuring the required capacity as the sample loop 23 also exists. Features of the sample injecting device provided in the described documents are all applicable to the sample injecting device of the present invention.

The embodiment is only an example of the present invention and can be appropriately varied or modified within the principle of the present invention. Apparently, the variations or modifications also fall within the protection scope of the present invention.

What is claimed is:

1. A sample injecting device, comprising:
   a sample loop for a measurement of a sample, comprising a needle at a front end for an injection of the sample;
   an injection port, comprising an opening for insertion of the vertically descending needle, and injecting the sample drawn in by the needle into a flow path for an analysis;
   a setting unit, selecting, from multiple alternative moving speeds, a descending speed of the needle moving from a defined position to the injection port when the sample is injected; and
   a controlling unit, controlling a descending movement of the needle according to the descending speed selected by the setting unit.

2. The sample injecting device according to claim 1, further comprising:
   a cleaning mechanism for cleaning the needle, and a cleaning procedure-setting unit for setting cleaning procedures of the cleaning mechanism.

3. The sample injecting device according to claim 2, wherein
   the descending speed of the needle is determined by setting the cleaning procedures.

4. The sample injecting device according to claim 1, wherein
   the descending speed of the needle during the movement from the defined position to the injection port is lower when the needle is close to one side of the injection port.

5. An analysis device, comprising the sample injecting device according to claim 1, wherein
   one of conditions for analyzing the sample is to set the descending speed of the needle.

\* \* \* \* \*